(12) United States Patent
Pluto et al.

(10) Patent No.: US 8,318,142 B2
(45) Date of Patent: Nov. 27, 2012

(54) METHOD OF STIMULATING HAIR GROWTH

(75) Inventors: Robin L. Pluto, Bloomfield Hills, MI (US); Susan B. Meklir, Bloomfield Hills, MI (US)

(73) Assignee: Renew Hair & Skin Center, LLC, Bingham Farms, MI (US)

( * ) Notice: Subject to any disclaimer, the term of this patent is extended or adjusted under 35 U.S.C. 154(b) by 88 days.

(21) Appl. No.: 13/036,505

(22) Filed: Feb. 28, 2011

(65) Prior Publication Data

US 2012/0220920 A1 Aug. 30, 2012

(51) Int. Cl.
*A61K 9/00* (2006.01)
*A61K 9/02* (2006.01)

(52) U.S. Cl. ........................ 424/70.1; 424/401

(58) Field of Classification Search .................. None
See application file for complete search history.

(56) References Cited

U.S. PATENT DOCUMENTS 7,722,655 B2  5/2010 Lee
2006/0129209 A1*  6/2006 McDaniel ................ 607/88

OTHER PUBLICATIONS

Gail Zimmerman, "A Renewed You Low Level Laser Therapy (LLLT) offers new hope for hair loss", Detroit Jewish News, Feb. 6, 2011, pp.26-29, Jewish Renaissance media Publication.

* cited by examiner

*Primary Examiner* — Susan Tran
(74) *Attorney, Agent, or Firm* — Quinn Law Group, PLLC

(57) ABSTRACT

A method of stimulating growth of a hair shaft from a hair follicle on a scalp of a human includes supplying a hair growth system. The hair growth system includes a vitamin complex ingestible by the human, a cleansing agent suitable for washing the scalp at least once every 48 hours and substantially free from each of sodium lauryl sulfate, palmitoyl ethanolamide, and dehydroepiandrosterone, and a plurality of laser diodes disposed in a fixture. The fixture is configured for surrounding the scalp and applying electromagnetic radiation to the scalp. The method also includes applying electromagnetic radiation having a wavelength of from about 380 nm to about 1,000 nm to the scalp at a radiant flux of from about 600 nW to about 700 nW via the plurality of laser diodes to stimulate growth of the hair shaft from the hair follicle. A hair growth system is also disclosed.

16 Claims, 2 Drawing Sheets

METHOD OF STIMULATING HAIR GROWTH

TECHNICAL FIELD

The present disclosure generally relates to hair growth, and more specifically, to a method and hair growth system for stimulating growth of a hair shaft on a scalp.

BACKGROUND

Hair growth on a scalp of a human occurs as a hair shaft emerges from a hair follicle. More specifically, hair growth may be characterized by three phases of a hair growth cycle. The hair shaft actively grows, i.e., lengthens and thickens, during the anagen phase of the hair growth cycle. The hair shaft stops growing during the transitional catogen phase, and rests during the telogen phase of the hair growth cycle. The hair shaft is shed from the scalp at the end of the telogen phase and replaced by a new hair shaft from the same hair follicle, and the hair growth cycle starts again. Any disruption in the aforementioned hair growth cycle caused by, for example, aging, stress, drugs, disease, hormonal fluctuations, and/or nutritional changes, may lead to hair loss.

SUMMARY

A method of stimulating growth of a hair shaft from a hair follicle on a scalp of a human includes supplying a hair growth system. The hair growth system includes a vitamin complex ingestible by the human, a cleansing agent suitable for washing the scalp at least once every 48 hours and substantially free from each of sodium lauryl sulfate, palmitoyl ethanolamide, and dehydroepiandrosterone, and a plurality of laser diodes disposed in a fixture. The fixture is configured for surrounding the scalp and applying electromagnetic radiation to the scalp. The method also includes applying electromagnetic radiation having a wavelength of from about 380 nm to about 1,000 nm to the scalp at a radiant flux of from about 600 nW to about 700 nW via the plurality of laser diodes to stimulate growth of the hair shaft from the hair follicle.

In one embodiment, the method includes microscopically analyzing the scalp, and supplying a hair growth system. The hair growth system includes a protein regimen, wherein the protein regimen is orally ingestible by the human at least once every 24 hours and includes a nutrient selected from the group of fatty acids, proteins, and combinations thereof. The hair growth system also includes a vitamin complex orally ingestible by the human once every 24 hours and including about 1,050 micrograms of vitamin B7, about 10,000 international units of vitamin A, about 400 international units of vitamin E, about 1,000 micrograms of folic acid, about 500 micrograms of vitamin C, about 25 milligrams of vitamin B1, about 25 milligrams of vitamin B2, about 50 milligrams of niacin, about 25 milligrams of vitamin B6, about 125 micrograms of vitamin B12, about 125 milligrams of pantothenic acid, about 50 milligrams of choline bitartrate, about 50 milligrams of inositol, and about 25 milligrams of para-aminobenzoic acid. In addition, the hair growth system includes a cleansing agent suitable for washing the scalp at least once every 48 hours and substantially free from each of sodium lauryl sulfate, palmitoyl ethanolamide, and dehydroepiandrosterone. Further, the hair growth system includes a conditioning agent, wherein the conditioning agent is suitable for conditioning the scalp and is substantially free from each of sodium lauryl sulfate, palmitoyl ethanolamide, and dehydroepiandrosterone. The hair growth system also includes a plurality of laser diodes disposed in a fixture, wherein the fixture is configured for surrounding the entire scalp and applying electromagnetic radiation to the scalp. In addition, the method includes applying electromagnetic radiation having a wavelength of from about 380 nm to about 1,000 nm to the scalp at a radiant flux of from about 635 nW to about 670 nW via the plurality of laser diodes for a duration of about 1 hour at an application frequency of from 1 time to 4 times per 7 days over a time period of about 1 year to stimulate growth of the hair shaft from the hair follicle.

A hair growth system for stimulating growth of a hair shaft from a hair follicle on a scalp of a human includes a vitamin complex ingestible by the human, a cleansing agent, wherein the cleansing agent is suitable for washing the scalp at least once every 48 hours and substantially free from each of sodium lauryl sulfate, palmitoyl ethanolamide, and dehydroepiandrosterone, and a plurality of laser diodes disposed in a fixture. The fixture is configured for surrounding the scalp and applying electromagnetic radiation having a wavelength of from about 380 nm to about 1,000 nm to the scalp at a radiant flux of from about 600 nW to about 700 nW to stimulate growth of the hair shaft from the hair follicle.

The method and hair growth system stimulate growth of the hair shaft from the hair follicle on the scalp. As such, the method and hair growth system increase a quantity and quality of hair shafts on the scalp and minimize loss of hair shafts from the scalp of the human. For example, the method and hair growth system stimulate the growth of new and existing hair shafts on the scalp of the human. Further, the method does not require maintenance pharmaceuticals and/or lifelong treatments, and is effective for hair shafts and scalps having any pigmentation. In addition, the method is painless and requires no recovery time. Further, the method induces no initial shedding of hair shafts from the scalp and produces no side effects. The method and hair growth system also promote a first phase of hair shaft growth from the hair follicle and increase a number of hair shafts emerging from a single hair follicle. As such, individual hair shafts gain volume and the scalp of the human exhibits increased coverage by hair shafts.

The above features and advantages and other features and advantages of the present disclosure are readily apparent from the following detailed description of the best modes for carrying out the disclosure when taken in connection with the accompanying drawings.

DETAILED DESCRIPTION

Figure 1:
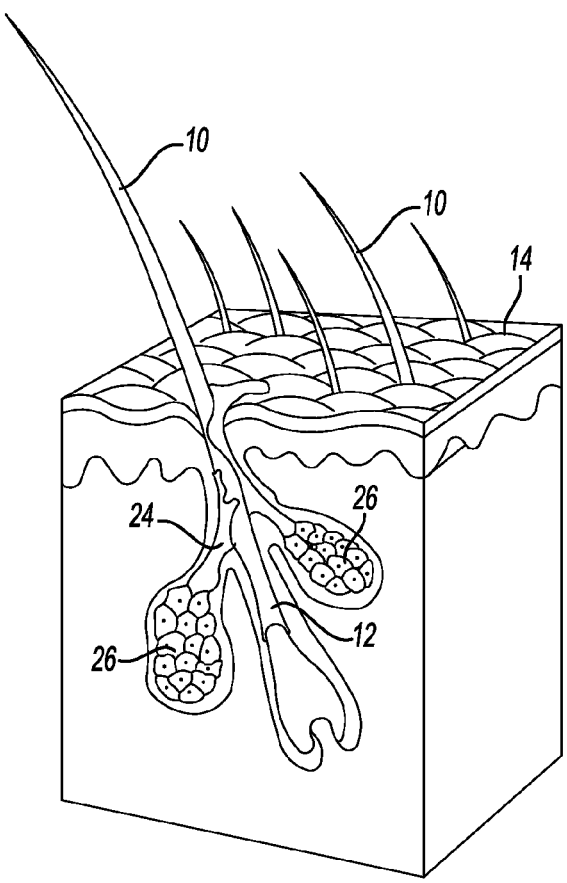
FIG. 1 is a schematic cross-sectional perspective illustration of a hair shaft growing from a hair follicle on a scalp of a human.

Referring to the Figures, wherein like reference numerals refer to like elements, a method of stimulating growth of a hair shaft 10 from a hair follicle 12 on a scalp 14 of a human 16 is described with reference to FIGS. 1 and 2. Further, a hair growth system for stimulating growth of the hair shaft 10 from the hair follicle 12 on the scalp 14 of the human 16 is shown generally at 18 in FIG. 3. The method and hair growth system 18 may be useful for growing a plurality of hair shafts 10 (FIG. 1) on the scalp 14 of the human 16. For example, the method and hair growth system 18 may be useful for growing hair shafts 10 to cover thinning or balding portions of the scalp 14. However, the method and hair growth system 18 may also be useful for non-human applications including stimulating growth of hair shafts 10 of other mammals, e.g., mice.

Figure 2:
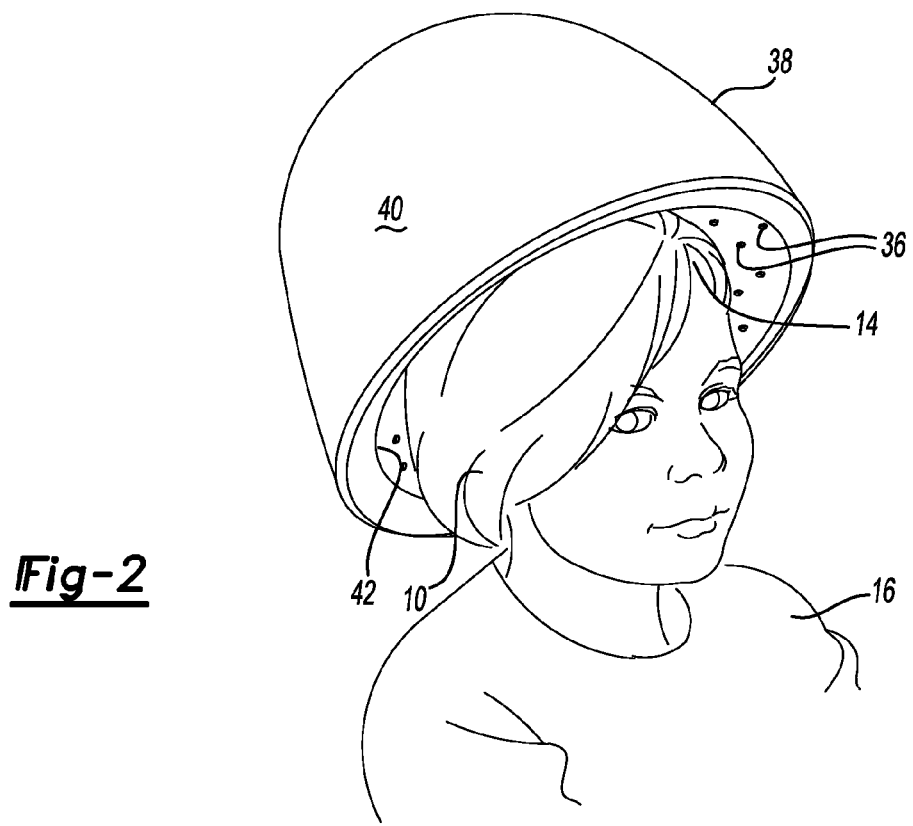
FIG. 2 is a schematic perspective illustration of a method of applying electromagnetic radiation to the scalp of FIG. 1.
Figure 3:
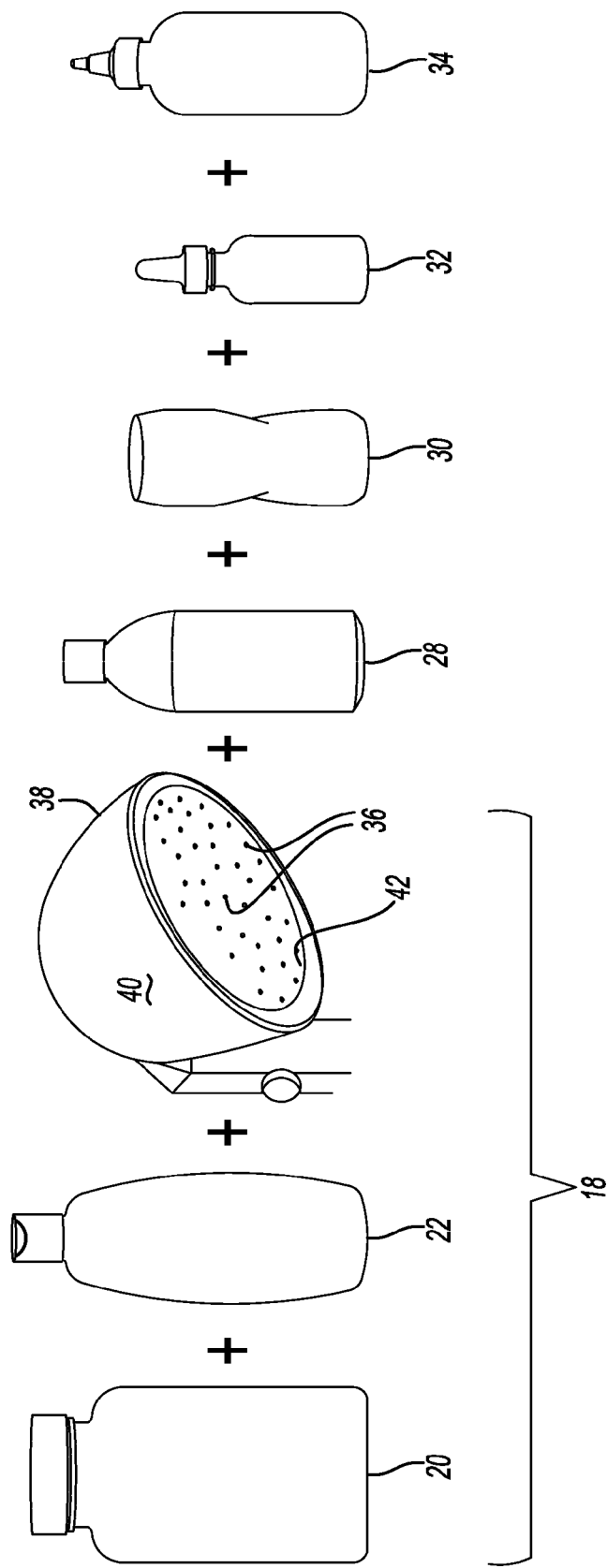
FIG. 3 is a schematic perspective illustration of a hair growth system for stimulating growth of the hair shaft of FIG. 1.

Referring now to FIGS. 2 and 3, the method includes supplying a hair growth system 18 (FIG. 3). Supplying may include providing and/or administering the hair growth system 18 to the human 16 (FIG. 2). As shown in FIG. 3, the hair growth system 18 includes a vitamin complex 20 ingestible by the human 16. For example, the vitamin complex 20 may be orally ingestible by the human 16 once every 24 hours. The vitamin complex 20 may nourish the hair shaft 10 during growth, as set forth in more detail below.

The vitamin complex 20 may include vitamin B7, vitamin A, vitamin E, folic acid, vitamin C, vitamin B1, vitamin B2, niacin, vitamin B6, vitamin B12, pantothenic acid, choline bitartrate, inositol, and para-aminobenzoic acid. More specifically, the vitamin complex 20 may include from about 750 micrograms to about 1,250 micrograms, e.g., about 900 micrograms to about 1,100 micrograms, of vitamin B7, wherein 1 microgram (μg or mcg) is equal to one millionth, i.e., $1\times10^{-6}$, of a gram. Vitamin B7 i.e., biotin or vitamin H, may stimulate and nourish cell (not shown) growth within the hair shaft 10 and assist in cell growth and fatty acid production and metabolism within the human 16. Therefore, at amounts of less than about 750 micrograms and/or greater than about 1,250 micrograms of vitamin B7, the vitamin complex 20 may not promote cell growth within the hair shaft 10. In one embodiment, the vitamin complex 20 may include about 1,050 micrograms of vitamin B7.

In addition, the vitamin complex 20 may include from about 8,000 international units to about 12,000 international units, e.g., about 9,000 international units to about 11,000 international units, of vitamin A, wherein an international unit is a measure of biological activity of a vitamin as defined by an international standard so that 1 international unit of one vitamin has the same effect on the human 16 as 1 international unit of another vitamin. The international unit (IU) may also be referred to as United States Pharmacopeia (USP). Vitamin A may protect the hair follicle 12 from damage by free radicals and may minimize dryness and breakage of the hair shaft 10. Therefore, at amounts of less than about 8,000 international units and/or greater than about 12,000 international units of vitamin A, the vitamin complex 20 may not protect the hair shaft 10. In one embodiment, the vitamin complex 20 may include about 10,000 international units of vitamin A.

The vitamin complex 20 may also include from about 200 international units to about 600 international units, e.g., about 300 international units to about 500 international units, of vitamin E. Vitamin E may provide dimensional stability to cell membranes (not shown) of the hair shaft 10 and hair follicle 12. Therefore, at amounts of less than about 200 international units and/or greater than about 600 international units of vitamin E, the vitamin complex 20 may not protect the hair shaft 10 and/or hair follicle 12 during growth and the hair shaft 10 may be brittle or mal-formed. In one embodiment, the vitamin complex 20 may include about 400 international units of vitamin E.

The vitamin complex 20 may also include from about 600 micrograms to about 1,400 micrograms, e.g., about 800 micrograms to about 1,200 micrograms, of folic acid. Folic acid, which is a synthesized form of folate, may promote and maintain cell division and growth within the hair follicle 12. Therefore, at amounts of less than about 600 micrograms and/or greater than about 1,400 micrograms of folic acid, the vitamin complex 20 may not protect nourish growth of the hair shaft 10 within the hair follicle 12. In one embodiment, the vitamin complex 20 may include about 1,000 micrograms of folic acid.

With continued reference to the vitamin complex 20, the vitamin complex 20 may further include from about 300 milligrams to about 700 milligrams, e.g., from about 400 milligrams to about 600 milligrams, of vitamin C, wherein 1 milligram (mg) is equal to $1\times10^{-3}$ grams. Vitamin C may contribute to and maintain collagen around the hair follicle 12, and may also protect against cellular damage from free radicals. As such, vitamin C may protect the hair shaft 10 from breakage or end-splitting. At amounts of less than about 300 milligrams and/or greater than about 700 milligrams of vitamin C, the vitamin complex 20 may not minimize cellular damage within the scalp 14. In one embodiment, the vitamin complex 20 may include about 500 milligrams of vitamin C.

The vitamin complex 20 may further include from about 12 milligrams to about 35 milligrams, e.g., from about 20 milligrams to about 30 milligrams, of vitamin B1. Vitamin B1 may aid in protein-building processes within the human 16 and therefore may contribute to growth of hair shafts 10 having excellent volume, shine, and texture. Therefore, at amounts of less than about 12 milligrams and/or greater than about 35 milligrams of vitamin B1, the vitamin complex 20 may not nourish and stimulate growth of hair shafts 10 having desired volume and/or capability to adequately cover the scalp 14. In one embodiment, the vitamin complex 20 may include about 25 milligrams of vitamin B1.

In addition, the vitamin complex 20 may include from about 15 milligrams to about 35 milligrams, e.g., from about 20 milligrams to about 30 milligrams, of vitamin B2. Vitamin B2, i.e., riboflavin, may act as an antioxidant and protect the hair shaft 10 from cellular damage caused by free radicals. In addition, vitamin B2 may work together with, e.g., activate, other constituents of the vitamin complex 20, such as vitamin B6 and niacin. Therefore, at amounts of less than about 15 milligrams and/or greater than about 35 milligrams of vitamin B2, the vitamin complex 20 may not minimize cellular damage within the scalp 14. In one embodiment, the vitamin complex 20 may include about 25 milligrams of vitamin B2.

In addition, the vitamin complex 20 may include from about 40 milligrams to about 60 milligrams, e.g., from about 45 milligrams to about 55 milligrams, of niacin. Niacin, i.e., vitamin B3, may dilate blood vessels and capillaries in the scalp 14 and thereby increase blood circulation to the scalp 14 to stimulate growth of the hair shaft 10. Therefore, at amounts of less than about 40 milligrams and/or greater than about 60 milligrams of niacin, the vitamin complex 20 may not contribute to optimal blood circulation to the hair follicle 12 of the scalp 14. In one embodiment, the vitamin complex 20 may include about 50 milligrams of niacin.

The vitamin complex 20 may further include from about 15 milligrams to about 35 milligrams, e.g., from about 20 milligrams to about 30 milligrams, of vitamin B6. Vitamin B6 may assist with amino acid conversion within the human 16, metabolism of fatty acids, and regulation of oil flow to the scalp 14. Therefore, at amounts of less than about 15 milligrams and/or greater than about 35 milligrams of vitamin B6, the vitamin complex 20 may not nourish the scalp 14 sufficiently to promote growth of the hair shaft 10. In one embodiment, the vitamin complex 20 may include about 25 milligrams of vitamin B6.

Further, the vitamin complex 20 may include from about 75 micrograms to about 175 micrograms, e.g., about 100 micrograms to about 150 micrograms, of vitamin B12. Vitamin B12 may promote and regenerate red blood cells (not shown) within the human 16, which may in turn contribute to a virile hair follicle 12 and scalp 14. Therefore, at amounts of less than about 75 micrograms and/or greater than about 175 micrograms of vitamin B12, the vitamin complex 20 may not sufficiently nourish the hair follicle 12 and/or scalp 14 of the human 16 to stimulate growth of the hair shaft 10. In one embodiment, the vitamin complex 20 may include about 125 micrograms of vitamin B12.

Further, the vitamin complex 20 may include from about 75 milligrams to about 175 milligrams, e.g., about 100 milligrams to about 150 milligrams, of pantothenic acid. Pantothenic acid, i.e., vitamin B5, may cooperate with folic acid to provide brightness to the hair shaft 10. Therefore, at amounts of less than about 75 milligrams and/or greater than about 175 milligrams of pantothenic acid, the vitamin complex 20 may not assist in releasing energy from food and/or other constituents of the vitamin complex 20 during ingestion and digestion within the human 16. In one embodiment, the vitamin complex 20 may include about 125 milligrams of pantothenic acid.

The vitamin complex 20 may additionally include from about 40 milligrams to about 60 milligrams, e.g., about 45 milligrams to about 55 milligrams, of choline bitartrate. Choline bitartrate may nourish the hair follicle 12 and promote healthy cell membranes (not shown) within the scalp 14 and hair follicle 12. Therefore, at amounts of less than about 40 milligrams and/or greater than about 60 milligrams of choline bitartrate, the vitamin complex 20 may not promote hair follicles 12 capable of supporting growth of the hair shaft 10. In one embodiment, the vitamin complex 20 may include about 50 milligrams of choline bitartrate.

The vitamin complex 20 may additionally include from about 40 milligrams to about 60 milligrams, e.g., about 45 milligrams to about 55 milligrams, of inositol. Inositol may nourish the cell membranes (not shown) of the hair follicle 12 and promote healthy cell membranes within the scalp 14. Inositol may also act as an antioxidant and protect the hair shaft 10 and hair follicle 12 from cellular damage from free radicals. Therefore, at amounts of less than about 40 milligrams and/or greater than about 60 milligrams of inositol, the vitamin complex 20 may not promote hair follicles 12 capable of supporting growth of the hair shaft 10. In one embodiment, the vitamin complex 20 may include about 50 milligrams of inositol.

In addition, the vitamin complex 20 may include from about 15 milligrams to about 35 milligrams, e.g., about 20 milligrams to about 30 milligrams, of para-aminobenzoic acid. Para-aminobenzoic acid may arrest loss of the hair shaft 10 from the hair follicle 12. Therefore, at amounts of less than about 15 milligrams and/or greater than about 35 milligrams of para-aminobenzoic acid, the vitamin complex 20 may not reduce shedding of the hair shaft 10 from the scalp 14 of the human 16. In one embodiment, the vitamin complex 20 may include about 25 milligrams of para-aminobenzoic acid.

The vitamin complex 20 may have any form. For example, the vitamin complex 20 may be orally ingestible by the human 16 as one individual tablet, cap, or pill, as a plurality of tablets, caps, or pills, and/or in powder or liquid form. A suitable vitamin complex 20 includes Swanson® Super Stress B-Complex with Vitamin C, Swanson® Premium Biotin, Swanson® Premium Vitamin A, Swanson® Premium Natural Vitamin E, and Swanson® Premium Folic Acid, each commercially available from Swanson Health Products of Fargo, N.D.

Referring again to FIG. 3, the hair growth system 18 further includes a cleansing agent 22 suitable for washing the scalp 14 at least once every 48 hours. The scalp 14 may be washed by the cleansing agent 22 more frequently, e.g., once or twice every 24 hours. The cleansing agent 22 may be a shampoo and include soaps, surfactants, and/or detergents for washing the scalp 14 (FIG. 1) and/or the hair shaft 10 (FIG. 1). Further, the cleansing agent 22 may remove excess sebum 24 (FIG. 1) from the scalp 14. Sebum 24, although produced naturally by the sebaceous glands 26 (FIG. 1) within the scalp 14 and important for healthy growth of the hair shaft 10, may block or clog the hair follicle 12 and therefore inhibit growth of the hair shaft 10. The cleansing agent 22 may include olive extract, wherein the olive extract may increase a tensile strength of the hair shaft 10. However, the cleansing agent 22 is substantially free from each of sodium lauryl sulfate, palmitoyl ethanolamide, and dehydroepiandosterone. Without intending to be limited by theory, sodium lauryl sulfate may block and/or shrink the hair follicle 12 after loss of the hair shaft 10 and thereby detract from new growth of the hair shaft 10. Further, palmitoyl ethanolamide and dehydroepiandosterone may induce shedding of the hair shaft 10 from the hair follicle 12. A suitable cleansing agent 22 includes Renew Volumizing Shampoo, commercially available from Renew Hair & Skin Center, LLC of Bingham Farms, Mich.

Referring again to FIG. 3, the hair growth system 18 may also include a conditioning agent 28, wherein the conditioning agent 28 is suitable for conditioning the scalp 14 (FIG. 1) and substantially free from each of sodium lauryl sulfate, palmitoyl ethanolamide, and dehydroepiandrosterone. The conditioning agent 28 may be formulated to complement the cleansing agent 22 and may be applied to the scalp 14 after the scalp 14 is washed by the cleansing agent 22. The conditioning agent 28 may condition, protect, and increase a volume of the hair shaft 10.

Referring again to FIG. 3, the hair growth system 18 may further include a protein regimen 30, wherein the protein regimen 30 is orally ingestible by the human 16 at least once every 24 hours and includes a nutrient selected from the group including fatty acids, proteins, and combinations thereof. The protein regimen 30 may be, for example, a protein-rich diet. That is, the human 16 (FIG. 2) may orally ingest an increased level of fatty acids, proteins, and/or combinations thereof as compared to a baseline diet of the human 16. Alternatively, the protein regimen 30 may include a protein supplement in the form of a pill, tablet, cap, powder, and/or liquid. Therefore, the human 16 may orally ingest the protein regimen 30 more frequently than once every 24 hours. For example, the protein regimen 30 may be part of each meal ingested by the human 16 so that the human 16 orally ingest the protein regimen 30 for from about 3 times to about 5 times every 24 hours. The protein regimen 30 may provide nutrients for cell development and promote growth of the structure of the hair shaft 10 from the hair follicle 12. The protein regimen 30 may be selected to complement the vitamin complex 20. That is, the protein regimen 30 may augment and/or cooperate with the vitamin complex 20. Further, the protein regimen 30 may be selected according to a weight and/or existing diet of the human 16. The protein regimen 30 and the vitamin complex 20 may be suitable for repeated ingestion by the human 16 over a time period of, for example, about 1 year, and the protein regimen 30 and the vitamin complex 20 may be suitable for concurrent ingestion by the human 16.

Suitable fatty acids for oral ingestion by the human 16 include, but are not limited to, omega-3 fatty acids such as alpha linolenic acid, omega-6 fatty acids such as linoleic acid, and omega-9 fatty acids such as oleic acid. Suitable sources of fatty acids include, but are not limited to, flaxseed oil, canola oil, soybean oil, and olive oil. Suitable proteins include, but are not limited to, proteins from animal sources such as meat, poultry, fish, eggs, milk, cheese, and yogurt, proteins from plant sources such as legumes, grains, nuts, and vegetables, and combinations thereof.

With continued reference to FIG. 3, the hair growth system 18 may also include a topical solution 32 including niacin, and a serum 34 including a plant-based stem cell extract. Each of the topical solution 32 and the serum 34 may be suitable for application to the scalp 14 (FIG. 2) from 1 time to 3 times every 24 hours. For example, one or both of the topical solution 32 and serum 34 may be applied to the scalp 14 after the scalp 14 is washed with the cleansing agent 22 and/or conditioned by the conditioning agent 28.

The topical solution 32 includes a niacin-based vasodilator and may also include fruit- and plant-extracts. As such, the topical solution 32 may promote blood circulation to the scalp 14 and hair follicle 12. Likewise, the serum 34 includes the plant-based stem cell extract, such as, but not limited to, stem cells of an apple tree. As used herein, the terminology "stem cells" refers to unprogrammed cells that can differentiate into cells having specific functions. Stem cells may replenish themselves through self-renewal and may generate differentiated cells. As such, the serum 34 may promote growth of the hair shaft 10 and may increase the lifespan of the hair follicle 12. That is, the serum 34 may allow the hair follicle 12 to remain an active site for emerging hair shafts 10 over multiple cycles of hair growth. The topical solution 32 and/or serum 34 may further include at least one of jojoba oil and emu oil. A suitable topical solution 32 and serum 34 includes Renew Topical Solution for Thinning Hair and Renew Serum, respectively, each commercially available from Renew Hair & Skin Center, LLC of Bingham Farms, Mich.

With continued reference to FIGS. 2 and 3, the hair growth system 18 also includes a plurality of laser diodes 36 disposed in a fixture 38, wherein the fixture 38 is configured for surrounding the scalp 14 and applying electromagnetic radiation to the scalp 14. For example, as shown in FIG. 2, the fixture 38 may be a hood configured for surrounding the entire scalp 14 of the human 16. The fixture 38 may be free-standing or may be attached to a chair configured to support the human 16. Further, the fixture 38 may be adjustable to accommodate humans 16 of varying heights. The fixture 38 may be configured for surrounding the entire scalp 14 of the human 16 at once rather than covering only a portion of the scalp 14 at one time. That is, the fixture 38 is differentiated from a panel or brush that may deliver electromagnetic radiation to only a portion of the scalp 14 at one time. As such, the fixture 38 defines an outer surface 40 and an inner surface 42 spaced apart from the outer surface 40 and configured for placement adjacent the scalp 14 of the human 16.

As best shown in FIG. 2, the fixture 38 may include from about 100 to about 170 laser diodes. For example, the fixture 38 may include more than about 120 laser diodes, and in one embodiment, the fixture 38 may include about 150 laser diodes. The plurality of laser diodes 36 may extend from the inner surface 42 of the fixture 38 and may be disposed in a random arrangement over substantially the entire inner surface 42. Further, the plurality of laser diodes 36 may be certified medical-grade or industrial-grade laser diodes 36 rather than cosmetic-grade laser diodes 36. As such, the plurality of laser diodes 36 may have a mean time before failure of from about 5,000 hours to about 10,000 hours. Further, the plurality of laser diodes 36 may have a temperature rating of about 60° C.

With continued reference to FIG. 2, the fixture 38 is configured for applying electromagnetic radiation having a wavelength of from about 380 nm to about 1,000 nm to the scalp at a radiant flux of from about 600 nW to about 700 nW to stimulate growth of the hair shaft 10 (FIG. 1) from the hair follicle 12 (FIG. 1), wherein 1 nm (nanometer) is equal to $1 \times 10^{-9}$ meters and 1 nW (nanowatt) is equal to $1 \times 10^{-9}$ watts. As used herein, the terminology radiant flux refers to radiant power of the fixture 38, i.e., radiant power per unit time. More specifically, the plurality of laser diodes 36 applies the electromagnetic radiation to the scalp 14. The electromagnetic radiation may be characterized as radiation in the visible light spectrum and/or infrared light spectrum. In addition, since the radiant flux is limited to from about 600 nW to about 700 nW, the plurality of laser diodes 36 of the fixture 38 may apply low-level laser therapy (LLLT) to the scalp 14.

Referring again to FIG. 2, the method further includes applying electromagnetic radiation having a wavelength of from about 380 nm to about 1,000 nm to the scalp 14 at a radiant flux of from about 600 nW to about 700 nW via the plurality of laser diodes 36 to stimulate growth of the hair shaft 10 (FIG. 1) from the hair follicle 12 (FIG. 1). In one embodiment, electromagnetic radiation described above may be applied to the scalp 14 at a radiant flux of from about 635 nW to about 670 nW, e.g., about 650 nW.

As shown in FIG. 2, electromagnetic radiation may be applied to the scalp 14 via the plurality of laser diodes 36 by disposing the scalp 14 of the human 16 under the fixture 38 adjacent the inner surface 42 so that the fixture 38 surrounds the entire scalp 14. The plurality of laser diodes 36 may then be energized, e.g., by an electrical current, and thereby apply the aforementioned electromagnetic radiation to the scalp 14.

Electromagnetic radiation may be applied to the scalp 14 for a duration of about 0.5 hours to about 1.5 hours, e.g., about 1 hour, at least once per 7 days. That is, the aforementioned electromagnetic radiation may be applied to the scalp 14 for about 1 hour every week. Alternatively, electromagnetic radiation may be applied to the scalp 14 more frequently, e.g., about 2 times to 3 times for about 1 hour every 7 days. In addition, electromagnetic radiation may be applied to the scalp 14 over a time period of at least 6 months. For example, electromagnetic radiation may be applied to the scalp 14 for a time period of about 1 year. Therefore, in one embodiment, the method may include applying electromagnetic radiation having a wavelength of from about 380 nm to about 1,000 nm to the scalp 14 at a radiant flux of from about 635 nW to about 670 nW via the plurality of laser diodes 36 for a duration of about 1 hour at an application frequency of from 1 time to 4 times per 7 days over a time period of about 1 year to stimulate growth of the hair shaft 10 from the hair follicle 12. Therefore, the method does not require maintenance pharmaceuticals and/or lifelong treatments, but is rather finite. After about 1 year, maintenance applications of electromagnetic radiation may be desired. For example, electromagnetic radiation may be applied for a duration of about 1 hour at an application frequency of 1 time every 30 days, 45 days, or 6 months, for a time period of about an additional year to continue to stimulate growth of the hair shaft 10 from the hair follicle 12 according to desired growth of hair shafts 10 on the scalp 14 of the human 16.

The method may further include, prior to applying electromagnetic radiation, microscopically analyzing the scalp 14. For example, the scalp 14 may be analyzed under a microscope (not shown) at a magnification of about 500%. The scalp 14 may be microscopically analyzed to verify the presence of viable hair follicles 12 that may respond sufficiently to one or more of the protein regimen 30, vitamin complex 20, cleansing agent 22, conditioning agent 28, topical solution 32, serum 34, and/or application of electromagnetic radiation in the aforementioned wavelength at the aforementioned radiant flux so as to grow one or more hair shafts 10 from the hair follicle 12.

Applying electromagnetic radiation to the scalp 14, in combination with supplying the hair growth system 18, stimulates growth of the hair shaft 10 from the hair follicle 12 on the scalp 14. Further, the resulting quantity and quality of growth of the hair shaft 10 via use of the method and hair growth system 18 is comparatively greater than a quantity and quality of growth if only portions of the method and hair growth system 18 are utilized. For example, minimal growth of the hair shaft 10 may occur as a result of ingesting the vitamin complex 20 without application of electromagnetic radiation as set forth above. In contrast, supplying the hair growth system 18 in combination with applying electromagnetic radiation as set forth above, stimulates unexpected and excellent growth of the hair shaft 10 from the hair follicle 12 on the scalp 14. Similarly, the exact combination of constituents of the vitamin complex 20 as set forth above provides necessary nourishment for stimulating growth of the hair shaft 10. In contrast, other combinations of nutrients may not provide necessary nourishment and therefore may not stimulate growth of the hair shaft 10.

Consequently, the method and hair growth system 18 increase a quantity of hair shafts 10 on the scalp 14 and minimize loss of hair shafts 10 from the scalp 14 of the human 16. For example, the method and hair growth system 18 stimulate the growth of new and existing hair shafts 10 on the scalp 14 of the human 16. Further, the method does not require maintenance pharmaceuticals and/or lifelong treatments, and is effective for hair shafts 10 and scalps 14 having any pigmentation. In addition, the method is painless and requires no recovery time. The method induces no initial shedding of hair shafts 10 from the scalp 14 and produces no side effects. The method and hair growth system 18 also promote a first phase of hair shaft growth from the hair follicle 12 and increase a number of hair shafts 10 emerging from a single hair follicle 12. As such, individual hair shafts 10 gain volume and the scalp 14 of the human 16 exhibits increased coverage by hair shafts 10.

While the best modes for carrying out the disclosure have been described in detail, those familiar with the art to which this disclosure relates will recognize various alternative designs and embodiments for practicing the disclosure within the scope of the appended claims.

The invention claimed is:

1. A method of stimulating growth of a hair shaft from a hair follicle on a scalp of a human, the method comprising:
   supplying a hair growth system including;
      a vitamin complex ingestible by the human; wherein the vitamin complex is orally ingestible by the human once every 24 hours and includes:
         from about 750 micrograms to about 1,250 micrograms of vitamin B7;
         from about 8,000 international units to about 12,000 international units of vitamin A;
         from about 200 international units to about 600 international units of vitamin E;
         from about 600 micrograms to about 1,400 micrograms of folic acid;
         from about 300 milligrams to about 700 milligrams of vitamin C;
         from about 12 milligrams to about 35 milligrams of vitamin B1;
         from about 15 milligrams to about 35 milligrams of vitamin B2;
         from about 40 milligrams to about 60 milligrams of niacin;
         from about 15 milligrams to about 35 milligrams of vitamin B6;
         from about 75 micrograms to about 175 micrograms of vitamin B12;
         from about 75 milligrams to about 175 milligrams of pantothenic acid;
         from about 40 milligrams to about 60 milligrams of choline bitartrate;
         from about 40 milligrams to about 60 milligrams of inositol; and
         from about 15 milligrams to about 35 milligrams of para-aminobenzoic acid;
      a cleansing agent suitable for washing the scalp at least once every 48 hours and substantially free from each of sodium lauryl sulfate, palmitoyl ethanolamide, and dehydroepiandrosterone; and
      a plurality of laser diodes disposed in a fixture, wherein the fixture is configured for surrounding the scalp and applying electromagnetic radiation to the scalp; and
   applying electromagnetic radiation having a wavelength of from about 380 nm to about 1,000 nm to the scalp at a radiant flux of from about 600 nW to about 700 nW via the plurality of laser diodes to stimulate growth of the hair shaft from the hair follicle.

2. The method of claim 1, wherein the hair growth system further includes a protein regimen orally ingestible by the human at least once every 24 hours, wherein the protein regimen includes a nutrient selected from the group including fatty acids, proteins, and combinations thereof.

3. The method of claim 1, wherein the fixture includes from about 100 to about 170 laser diodes.

4. The method of claim 1, wherein electromagnetic radiation is applied to the scalp for a duration of from about 0.5 hours to about 1.5 hours at least once per 7 days.

5. The method of claim 4, wherein electromagnetic radiation is applied to the scalp over a time period of at least 6 months.

6. The method of claim 1, wherein the hair growth system further includes a topical solution suitable for application to the scalp from 1 time to 3 times every 24 hours.

7. The method of claim 6, wherein the topical solution includes niacin.

8. The method of claim 1, wherein the hair growth system further includes a serum suitable for application to the scalp from 1 time to 3 times every 24 hours and including a plant-based stem cell extract.

9. The method of claim 1, further including, prior to applying electromagnetic radiation, microscopically analyzing the scalp.

10. A method of stimulating growth of a hair shaft from a hair follicle on a scalp of a human, the method comprising:
   microscopically analyzing the scalp;
   supplying a hair growth system including;
      a protein regimen, wherein the protein regimen is orally ingestible by the human at least once every 24 hours and includes a nutrient selected from the group of fatty acids, proteins, and combinations thereof;
      a vitamin complex orally ingestible by the human once every 24 hours and including;
         about 1,050 micrograms of vitamin B7;
         about 10,000 international units of vitamin A;
         about 400 international units of vitamin E;
         about 1,000 micrograms of folic acid;
         about 500 micrograms of vitamin C;
         about 25 milligrams of vitamin B1;

about 25 milligrams of vitamin B2;
about 50 milligrams of niacin;
about 25 milligrams of vitamin B6;
about 125 micrograms of vitamin B12;
about 125 milligrams of pantothenic acid;
about 50 milligrams of choline bitartrate;
about 50 milligrams of inositol; and
about 25 milligrams of para-aminobenzoic acid;
a cleansing agent suitable for washing the scalp at least once every 48 hours and substantially free from each of sodium lauryl sulfate, palmitoyl ethanolamide, and dehydroepiandrosterone;
a conditioning agent, wherein the conditioning agent is suitable for conditioning the scalp and is substantially free from each of sodium lauryl sulfate, palmitoyl ethanolamide, and dehydroepiandrosterone; and
a plurality of laser diodes disposed in a fixture, wherein the fixture is configured for surrounding the entire scalp and applying electromagnetic radiation to the scalp; and
applying electromagnetic radiation having a wavelength of from about 380 nm to about 1,000 nm to the scalp at a radiant flux of from about 635 nW to about 670 nW via the plurality of laser diodes for a duration of about 1 hour at an application frequency of from 1 time to 4 times per 7 days over a time period of about 1 year to stimulate growth of the hair shaft from the hair follicle.

11. The method of claim 10, wherein the hair growth system further includes a topical solution including niacin, and a serum including a plant-based stem cell extract, and wherein each of the topical solution and the serum is suitable for application to the scalp from 1 time to 3 times every 24 hours.

12. A hair growth system for stimulating growth of a hair shaft from a hair follicle on a scalp of a human, the hair growth system comprising:
a vitamin complex ingestible by the human;
a cleansing agent, wherein the cleansing agent is suitable for washing the scalp at least once every 48 hours and substantially free from each of sodium lauryl sulfate, palmitoyl ethanolamide, and dehydroepiandrosterone; and
a plurality of laser diodes disposed in a fixture, wherein the fixture is configured for surrounding the scalp and applying electromagnetic radiation having a wavelength of from about 380 nm to about 1,000 nm to the scalp at a radiant flux of from about 600 nW to about 700 nW to stimulate growth of the hair shaft from the hair follicle, wherein the vitamin complex is orally ingestible by the human once every 24 hours and includes:
from about 750 micrograms to about 1,250 micrograms of vitamin B7;
from about 8,000 international units to about 12,000 international units of vitamin A;
from about 200 international units to about 600 international units of vitamin E;
from about 600 micrograms to about 1,400 micrograms of folic acid;
from about 300 milligrams to about 700 milligrams of vitamin C;
from about 12 milligrams to about 35 milligrams of vitamin B1;
from about 15 milligrams to about 35 milligrams of vitamin B2;
from about 40 milligrams to about 60 milligrams of niacin;
from about 15 milligrams to about 35 milligrams of vitamin B6;
from about 75 micrograms to about 175 micrograms of vitamin B12;
from about 75 milligrams to about 175 milligrams of pantothenic acid;
from about 40 milligrams to about 60 milligrams of choline bitartrate;
from about 40 milligrams to about 60 milligrams of inositol; and
from about 15 milligrams to about 35 milligrams of para-aminobenzoic acid.

13. The hair growth system of claim 12, further including a protein regimen, wherein the protein regimen is orally ingestible by the human at least once every 24 hours and includes a nutrient selected from the group including fatty acids, proteins, and combinations thereof.

14. The hair growth system of claim 13, further including a conditioning agent, wherein the conditioning agent is suitable for conditioning the scalp and substantially free from each of sodium lauryl sulfate, palmitoyl ethanolamide, and dehydroepiandrosterone.

15. The hair growth system of claim 14, further including a topical solution including niacin, and a serum including a plant-based stem cell extract, and wherein each of the the topical solution and the serum is suitable for application to the scalp from 1 time to 3 times every 24 hours.

16. The hair growth system of claim 12, wherein the vitamin complex includes;
about 1,050 micrograms of vitamin B7;
about 10,000 international units of vitamin A;
about 400 international units of vitamin E;
about 1,000 micrograms of folic acid;
about 500 micrograms of vitamin C;
about 25 milligrams of vitamin B1;
about 25 milligrams of vitamin B2;
about 50 milligrams of niacin;
about 25 milligrams of vitamin B6;
about 125 micrograms of vitamin B12;
about 125 milligrams of pantothenic acid;
about 50 milligrams of choline bitartrate;
about 50 milligrams of inositol; and
about 25 milligrams of para-aminobenzoic acid.

* * * * *